(12) United States Patent
Volker

(10) Patent No.: US 9,918,621 B2
(45) Date of Patent: Mar. 20, 2018

(54) SYSTEM FOR STORING AND APPLYING FLUSH SOLUTIONS

(71) Applicant: Manfred Volker, Blankenbach (DE)

(72) Inventor: Manfred Volker, Blankenbach (DE)

(*) Notice: Subject to any disclaimer, the term of this patent is extended or adjusted under 35 U.S.C. 154(b) by 0 days.

(21) Appl. No.: 14/950,286

(22) Filed: Nov. 24, 2015

(65) Prior Publication Data

US 2016/0256046 A1    Sep. 8, 2016

(30) Foreign Application Priority Data

Nov. 25, 2014    (DE) ................. 10 2014 017 402

(51) Int. Cl.
| | | |
|---|---|---|
| *A61B 1/12* | (2006.01) | |
| *A61B 90/70* | (2016.01) | |
| *A61M 5/14* | (2006.01) | |

(52) U.S. Cl.
CPC .............. *A61B 1/125* (2013.01); *A61B 90/70* (2016.02); *A61M 5/14* (2013.01); *A61M 2005/1403* (2013.01)

(58) Field of Classification Search
CPC .......... A61B 1/125; A61B 90/70; A61M 5/14; A61M 2005/1403
USPC ..... 134/166 C, 166 R, 167 C, 167 R, 168 C, 134/168 R, 169 A, 169 C, 169 R, 170, 134/171; 141/313; 210/636
See application file for complete search history.

(56) References Cited

U.S. PATENT DOCUMENTS

| | | |
|---|---|---|
| 6,096,007 A | 8/2000 | Haan et al. |
| 7,635,359 B2 | 12/2009 | Nakazawa et al. |
| 2002/0001537 A1* | 1/2002 | Hlebovy ............ A61B 1/00057 422/28 |

(Continued)

FOREIGN PATENT DOCUMENTS

| | | |
|---|---|---|
| DE | 1955538 | 12/1966 |
| DE | 3315031 A1 | 1/1985 |
| DE | 4121568 A1 | 10/1992 |

(Continued)

OTHER PUBLICATIONS

"Google search results.pdf", Sep. 30, 2016—search results from Google.com.*

*Primary Examiner* — Levon J Shahinian
(74) *Attorney, Agent, or Firm* — Greer, Burns & Crain, Ltd.

(57) ABSTRACT

The system for storing and applying flush solutions, preferably in the medical field such as for general and endoscopic operations, with a flush solution bag that is arranged in a rigid container, is characterized in that the rigid container has a swiveling lid with a connector receptacle, through which a bag connector is stuck, that can be mounted to the bag connector by means of a movable connector locking device and a holding slot arrangement, in that running through the bag connector is a filling line that is provided with a link connector that can be connected to a link connector of the mixing unit, in that the link connector of the mixing unit is covered by a swiveling concentrate flap in its closed state in such a manner that a tight flushing area is formed around the link connector, and in that a flush fluid line discharges into the link connector of the mixing unit in such a way that flushing fluid that can completely clean the link connector on the inside and outside can be conveyed into the flushing area.

10 Claims, 10 Drawing Sheets

(56) References Cited

U.S. PATENT DOCUMENTS

2006/0276762 A1* 12/2006 Nakazawa .......... A61M 1/0001
 604/319
2011/0042202 A1 2/2011 Pettee et al.

FOREIGN PATENT DOCUMENTS

| | | |
|---|---|---|
| DE | 4122171 A1 | 1/1993 |
| DE | 4137748 A1 | 5/1993 |
| DE | 4332070 A1 | 3/1995 |
| DE | 69318988 T2 | 3/1996 |
| DE | 19538818A11 | 4/1997 |
| DE | 19733278 A1 | 2/1999 |
| DE | 102009057562 A1 | 6/2011 |
| DE | 102010055781 A1 | 6/2012 |
| DE | 102011102662 A1 | 11/2012 |
| DE | 102012001879 A1 | 8/2013 |
| EP | 2689790 | 7/2012 |
| EP | 2674399 | 12/2013 |
| WO | 2005077335 A1 | 8/2005 |

\* cited by examiner

SYSTEM FOR STORING AND APPLYING FLUSH SOLUTIONS

FIELD OF THE INVENTION

The subject application relates to medical flushing solutions, and more particularly to a system for storing and applying flush solutions.

SUMMARY OF THE INVENTION

The object of this development is the preparation, storage and mobile application of locally produced flush solutions. A mobile fluid storage unit that is equipped with a sterile disposable article, exact volume determination and sterile removal and application is to allow simple and economical application.

In this process both flush solutions for endoscopic and general surgical operations, e.g., in gynecology, urology, arthroscopy through the use of Purisole, Ringer's, common salt concentrates, and also solutions for therapeutic applications can be produced.

An application of this development to other areas such as, e.g., veterinary medicine, in the laboratory or in biology and pharmaceutics as a high-purity flush fluid or also as a base medium for the production of medicines, cell cultures and the like is conceivable and practicable.

As a rule, medical flush solutions are further processed into flush solutions in a central production process, taking as a base substance distilled water that is produced in a central process, whereby the flush solutions must then be brought to the place of use with considerable logistics costs.

For medical use, for example, industrially produced flush solutions with 3 l, 5 l and 10 l volumes are provided to the hospital and temporarily or permanently stored with sub- stantial in-house, staff logistics operations.

These bag volumes are not sufficient for the duration of the operation or examination, for example, for bladder surgery with approximately 60-l flush fluid, so that a relief-person must be available outside the central OP area in order to provide, heat and hand over the bag.

Application is effected to some extent gravimetrically or also with pressure infusion cuffs. In addition, often expensive disposal articles such as, for example, pump segments or also bag warmers are required.

A crucial disadvantage during endoscopic examinations is the inability to see through free-floating tissue or pulsing flush fluid, because, for example, the required flush fluid pressure between 0.1 bar and 0.3 bar is not kept constant.

Generous flushing is necessary for an improvement in wound hygiene. This results in both personnel and material costs.

The regulative and normative requirements regarding the quality of the base substance water are thereby so high that until now it has not been possible to produce verifiable medical flush solutions locally, e.g., in a hospital, as needed.

On the one hand, it is the high microbiological requirements and, on the other hand, the necessary chemical requirements placed on the base substance water that stand in the way of verifiable and demonstrable, normative quality requirements of the local demand-driven production.

The decentralized production of medical flush solutions by hospital personnel demands reliable sequences both in the operation and also in the dependability of the technology with respect to the flush solution quality.

Necessary improvements, purpose and object of this invention are therefore an economical, user-friendly local production of a flush solution with low personnel deployment and a flush volume consistent with the examination or also with a plurality of operations.

Special significance is given to uninterrupted application without additional personnel effort while complying with the application temperature and hygiene of the solution.

A space-saving technology for the production of the flush solution and a mobile flush solution container should thereby be used, whereby said flush solution container contains the essential components for high hygiene, safety, simple operation and a constant flow and pressure for the application of the flush fluid.

It should be simple to dispose of residual quantities.

High availability of the devices during all measuring and monitoring tasks with respect to their intrinsic safety and an only remote failure probability are important in order under all circumstances to avoid a catastrophic effect for the patient and perfectly to monitor the quality or also toxicity of the created fluid in the guaranteed acceptance criteria.

This object is effectively solved according to the invention by using the combination of a reverse osmosis membrane and two additional filtering stages, for example, ultra or sterile filters, preferably as capillary membrane, for the production of the flush solution.

This filter combination and further constituents are called the filling station in the following.

For example, for the production of approximately 60 l of ready-to-use Purisole solution, approximately 56 l of sterile-filtered permeate is to be proportionally diluted or mixed with approximately 3.6 l of highly concentrated Purisole concentrate in such a manner that the resulting flush solution can be used for intra- and post-operative bladder irrigation without additional testing.

The aforementioned flush solution is representative, e.g., for Ringer's and/or other sodium chloride solutions that can be used particularly in the field of surgery, but also in other medical or named areas, whereby the concentrates and their mixture ratios must be adapted to the specific applications.

The described method and the components and volumes used are however not reduced to this. A large bandwidth of flush solutions can be produced conditional on the high-purity agents, exact mixing and dilution.

Advantageously, the germ growth of the concentrate is also virtually prevented due to the high concentration.

For the preparation of the flush solution, the concentrate container, which is advantageously executed as a bag, is hung on the prepared receptacles of the filling station concentrate scale and the mixing process is initiated. First the scale is thereby verified by means of the known bag weight.

The user brings about the filling-station-side links of both the concentrate bag and the still-to-be-described flush solution bag to self-cleaning, fool-proof link connectors of the filling station, which are executed in this application for example as flap solutions, but that can also be executed on the device side as flexible hose line.

With great advantage, a mobile flush solution container which preferably is formed as a pressurized container is equipped with an insertable sterile flush fluid bag that is filled with a correspondingly large volume.

The flush solution bag contains a non-detachable link connector that can be stuck through the locking lid of the pressurized container and fixed in place. The link connector can be provided with continuative flexible hose lines that are formed as filling or transfer lines, whereby the connector can, with advantage, also be executed as only a hose that selectively, and depending on the sterility requirements, can be used as both a filling hose and also as a transfer hose.

For the application of the flush fluid at the place of use, a transition system can, at the transfer link of the flush solution connector, be connected to, for example, an endoscopy system. A link to other systems common in surgery, for example, to flush-suction systems, is likewise practicable and possible.

The object of simple operation and application with a constant flush flow and pressure is solved in that compressed gas (air) is either preferably introduced into the pressurized container or also selectively introduced directly into the flush fluid bag.

With advantage the compressed gas regulation and monitoring are thereby arranged within the mobile flush solution container. Compressed gas generation and supply can, for example, be produced by an in-house source, or also by the device.

The proportioning of concentrate and permeate takes place by means of a concentrate scale and a flush solution container scale, whereby the concentrate scale in the filling station is verified each time the filled concentrate container is hung on.

For this purpose, the mobile flush solution container advantageously includes a scale that monitors the filing level and that, for safety reasons, is to be tested automatically by means of a reference weight.

For homogenization and tempering, high-purity or approximately sterile permeate is heated and mixed with metered-in concentrate in a mixing block.

Before the introduction into a sterile flush solution container/bag, a second sterile filtering of the mixed solution takes place.

The cleaning of the system or the germ prevention and reduction are executed by means of the combination of a slightly toxic disinfecting and cleaning agent based on citrate and by heating water, whereby both the primary and also the secondary side of the reverse osmosis are to be disinfected or cleaned, separately from one another, by means of an additional pump also without transmembrane flow.

In principle, all process-relevant data both from the operating computer and the protection computer are thereby acquired and, where appropriate, calculated. The measurement results are sent from the operating computer to the protection computer and from the protection computer to the operating computer. Each computer thereby compares the measurement results with its own and sends back a confirmation.

After the confirmation from the operating and protection computers, the data, together with a checksum, are written into the trend data memory, which can preferably be formed as EPROM, but also as some other storage medium.

The electronics of the mobile flush solution container can be operated by means of rechargeable batteries, and all required parameters and also their deviations, such as for example, weight, temperature and container pressure are displayed on the display of the mobile flush solution container.

Monitoring of the filling, proportionality and temperature, for example, takes place by producing a wireless data exchange between the filling station and the mobile flush solution container.

Further details and advantages are described in the figures depicted in the following.

DETAILED DESCRIPTION OF PREFERRED EMBODIMENTS

Figure 1A:
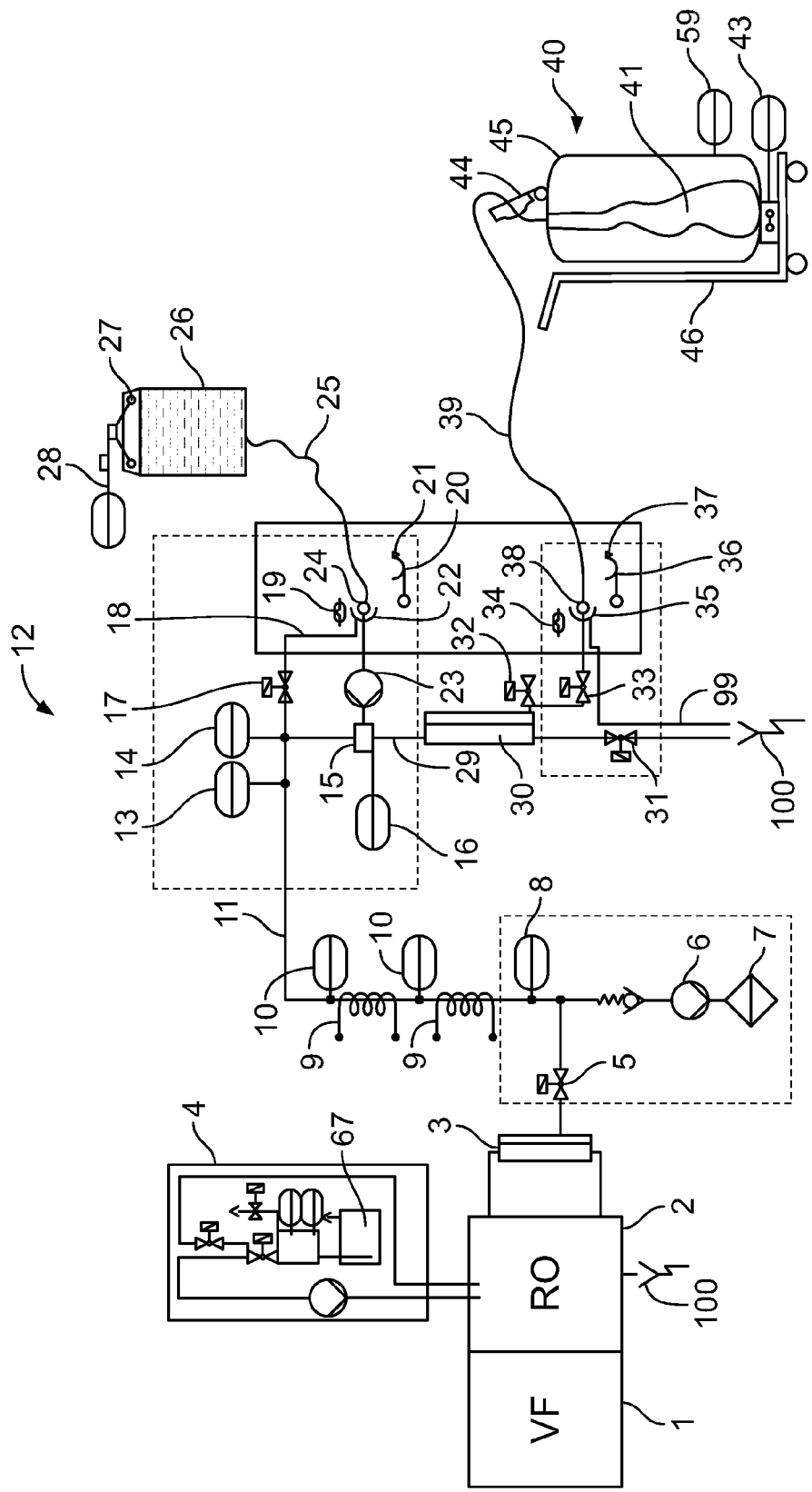
FIG. 1A is a schematic view a system for storing and applying flush solutions.
Figure 1B:
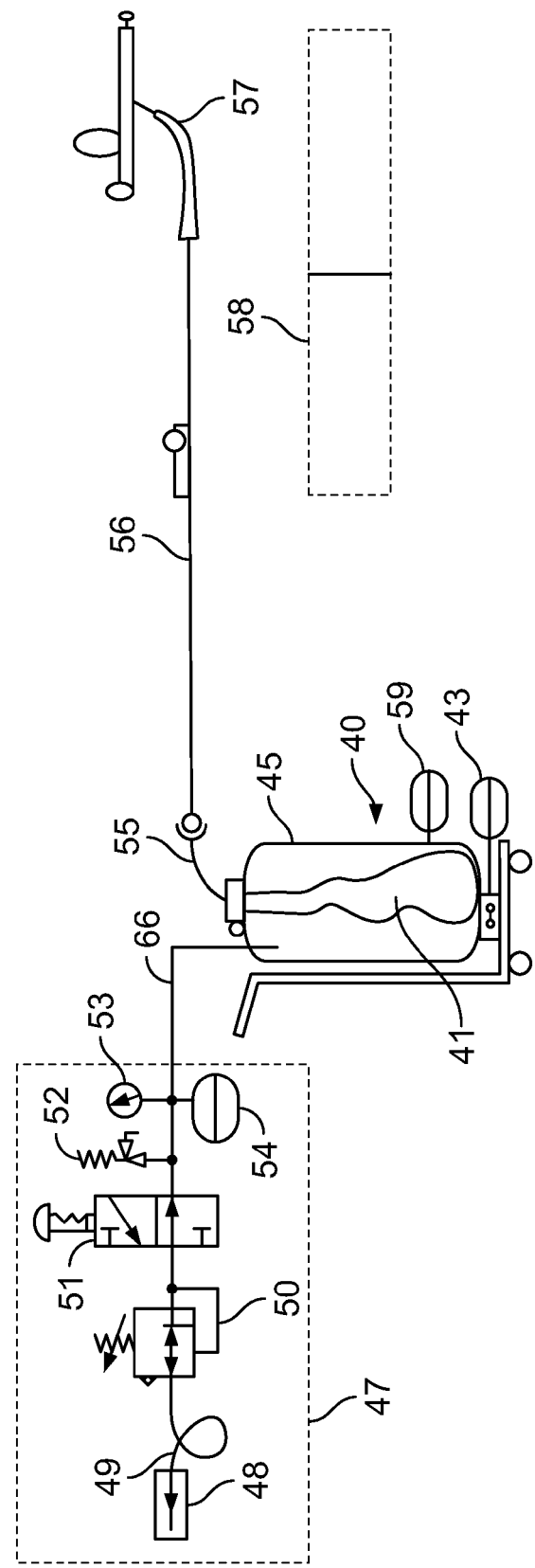
FIG. 1B is a schematic view of an endoscopic system.

FIG. 1 shows the entire preparation up to the point of application. The fluid to be prepared can be forwarded to the RO system (2) via, for example, optional preliminary filtration (1), which can be formed as particle and/or further filtering stages for the elimination of hardeners and chlorine. For the elimination of microbiological contamination, the RO system (2) contains, for example, a disinfection unit (4) with which chemothermal disinfection can be conducted without the involvement of the user. Canister (67) contains the disinfecting/cleaning agent that is used with advantage as a citrate-containing solution. The further function of mechanism (4) is derived from the depiction and is not further described here. Naturally hot cleaning of the RO system without the use of further disinfecting agent is possible.

The permeate created by the RO system (2) is circulated over the primary side of the filter (3). The permeate released by the RO controller (58) by means of non-depicted conductivity measurement reaches the secondary side of the filter (3) and then the mixing unit (12) via permeate release valve (5).

Permeate possibly already preheated by the RO system (2) is heated to the required flush solution temperature via the heater (9) and temperature regulator (8, 13). The permeate is supplied via line (11) to a mixing chamber (15) into which concentrate from bag (26) and line (25), the connector (24) and device-side link connector (22) is supplied by means of pump (23). The concentrate flap (20) is thereby opened, detector (19) reports "open" because magnet (21) has exceeded the required distance. The concentrate flush valve (17) is only opened when the flap (20) is closed and with correspondingly selected or preset flush programs in order to clean the link connector (22).

Concentrate bag (26), with its hangers (27), is hung into the corresponding hooks of the concentrate bag scale (28).

The second conductivity and temperature measurement (16) detects the corresponding values for reasons of redundancy. The flush fluid that has been homogeneously mixed and tempered by the chamber (15) reaches a second sterile filter (30) via line (29). Incorrect flush fluid is discarded to the drain (100) via the bypass valve (31).

With the valve (31) closed and the flush solution release valve (33) open, the flush fluid is directed via the device-side flush solution connector (35), the bag connector (38) connected thereto, line (39), to the mobile flush solution container (40) into which a sterile flush solution bag (82) is loaded. The possibility to remove a flush solution sample volume exists at the sampling point (32).

The mobile flush solution container contains a scale (43) that registers the respective filling level or the weight of the flush volume. Likewise a thermal sensor (59) is affixed in such a manner that the flush fluid temperature can be indirectly measured.

With the flush solution flap (36) closed and the selection and initiation of a corresponding flush program, the device-side connector (35) is flushed or disinfected with sterile fluid or cleaning solution, respectively, via flush drain (99).

The test of the filters (3/30) takes place with closed flaps (20/36) by feeding filtered air by means of air pump (6) and can selectively expose the secondary side of the filter (3) or the primary side of the filter (30) to air by means of a valve switch. The fluid is thereby partially displaced by the air. Due to the hydrophilic character of the filter membrane, given intact filter characteristics, only a very slight pressure drop will result which can be registered or monitored, as the case may be, by means of pressure sensor (14) and electronics (58).

This test can be used to verify or check, as the case may be, both the filters (3/30) and also the tightness of the flaps (20, 36).

FIG. 1 likewise schematically depicts a possible transfer of the flush fluid to an endoscopic system (57). Compressed air connector (48) can be linked to an in-house compressed gas source by means of flexible hose lines (49).

To guarantee a constant flush fluid flow, the pressure regulation unit (47) includes an adjustable pressure regulator (50), an emergency-off with mushroom button and forced venting (51), a manual pressure limiting valve (52), a manometer display (53), and an electronic pressure sensor (54) that, like all sensors and actuators, can be evaluated and depicted by means of redundant electronics (58).

The low-pressure regulating valve (50) can be adjusted only by means of a tool. The pressure regulation unit (47) can be designed for a regulation range from 0 to 0.5 bar and is adjusted for practical use to 0.3 bar feed pressure, for example, for prostate gland operations. The air regulated in this way is introduced into the pressurized container (45) via hose connection (66). The flush fluid in bag (82) is conveyed by the fed pressure via transfer link (55) and a suitable transition system (56) to the endoscopic system (57).

It shall be understood that units other than endoscopic systems can also be linked to system (56).

For the sake of completion, it is ascertained that a further sterile filter, not depicted here, would be connectable to line (55).

Likewise it would be possible to introduce the regulated compressed gas medium directly into the flush solution bag (41).

Figure 2A:
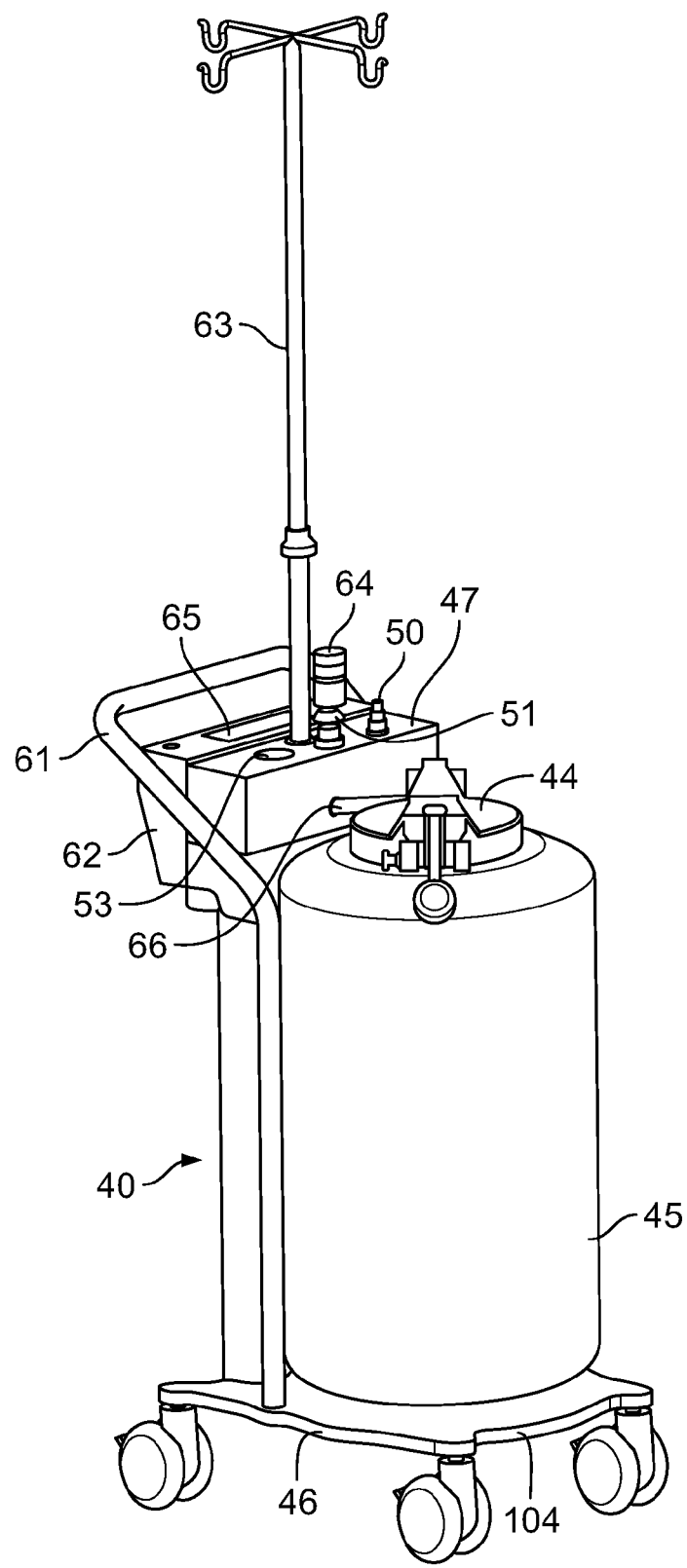
FIG. 2A is a view of a transport carriage.
Figure 2B:
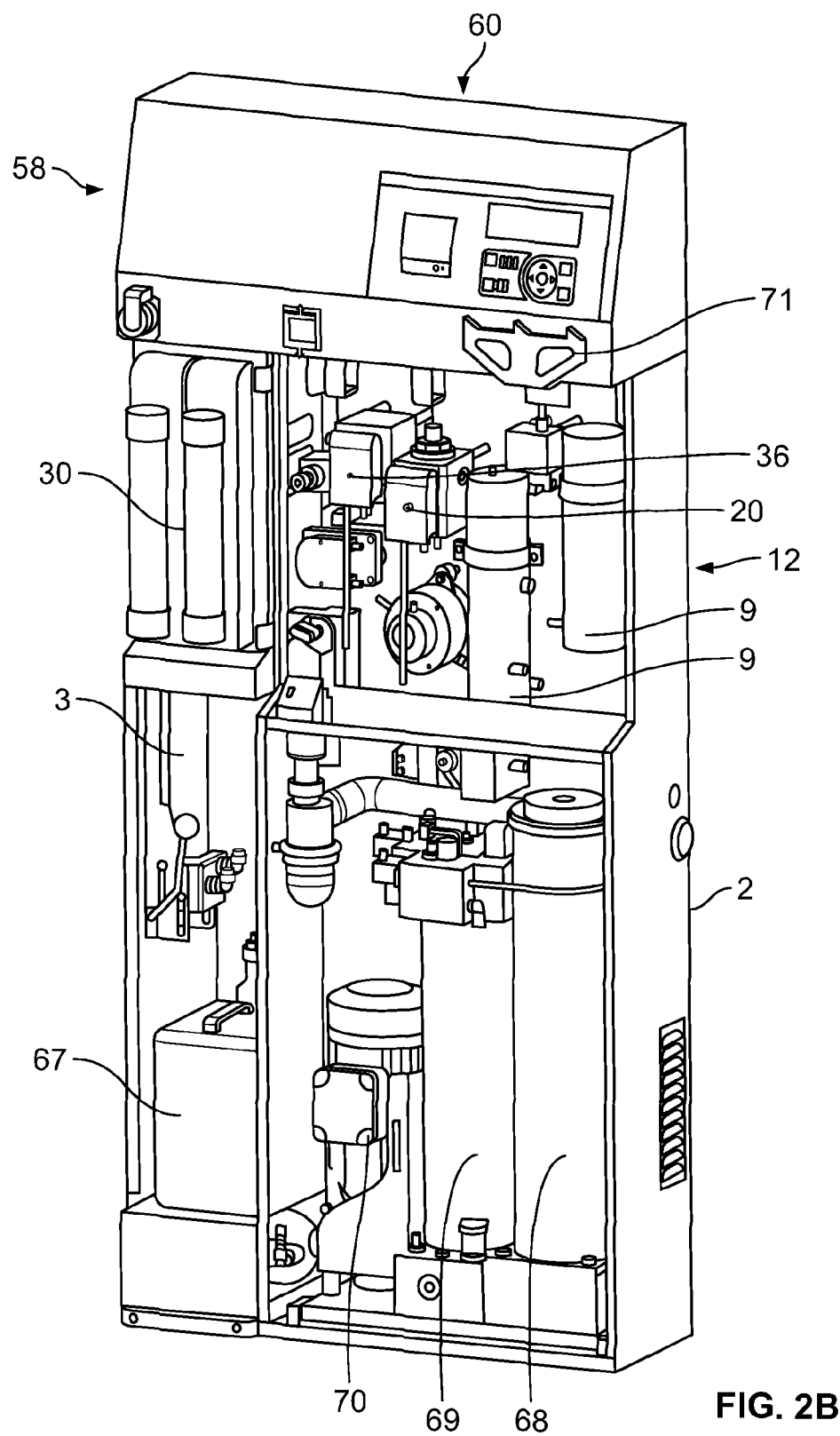
FIG. 2B is a view of a filling station.

FIG. 2 is a three-dimensional illustration of the complete unit of a mixing system and filling station. On the basis of the assumed spatially confined conditions in hospitals, the filling station (60) was designed to be as flat as possible in order not to interfere with the passageways in corridors or in rooms. This requires a vertical construction of the RO system (2) with membrane (68), feed tank (69) and pump (70). Also depicted is a cleaning canister (67).

The mixing unit (12) is affixed above the RO system, whereby in this drawing only the positions of the concentrate flap (20), the flush solution flap (36), the heater (9) and the sterile filter (30) are indicated in order to illustrate the handling, whereby the flaps are depicted here in the closed state.

Concentrate bag scale (28) is mounted underneath the electronics (58) and is depicted in the form of an extension piece (71) with holding hook for the concentrate bag.

Installation is flush with the wall at a suitable location at a corresponding height above the floor in order to guarantee communication, as later explained, and cleaning.

The mobile flush solution container (40) consists of a transport carriage (46) with push and pull handle (61), the pressurized container (45), a lid (44) and an infusion pole (63).

Constituents of the mobile flush solution container (40) are a pressure regulation unit (47), whose outlet discharges directly into the pressurized container (45) via a flexible hose connection (66), and electronics (62) with a communication display (65), for example, for the display of the filling level, temperature, compressed air and other relevant values, and a display light (64).

Communication between the flush solution container (40) and filing station (60) is effected wirelessly by means of sensors in the roller area underneath the bottom plate (104) of the transport carriage (40).

The detection of the park or docking position of the flush solution container (40) at the filling station (60) is given by the position of the preferably infrared sensors.

On the filling station side, a corresponding sensor is affixed at the same level. The docking angle and docking position at the filling station are thereby to be influenced by the selection and position of the sensors.

The mobile flush solution container (40) can be equipped with a rechargeable battery and/or a power supply; likewise isolation and/or the addition of a heating unit preferably as heating foil is possible for heating or loss-free storage of the heated flush fluid. The addition of an internal compressor as a pressure source is likewise possible and practicable.

The further components are explained to some extent from the depiction or are explained later. It shall be understood that shown here is a space-saving construction of the components whose arrangement can differ from that depicted and that is also conceivable in other embodiments. Likewise reference to the labeling was not made in all points.

Figure 3A:
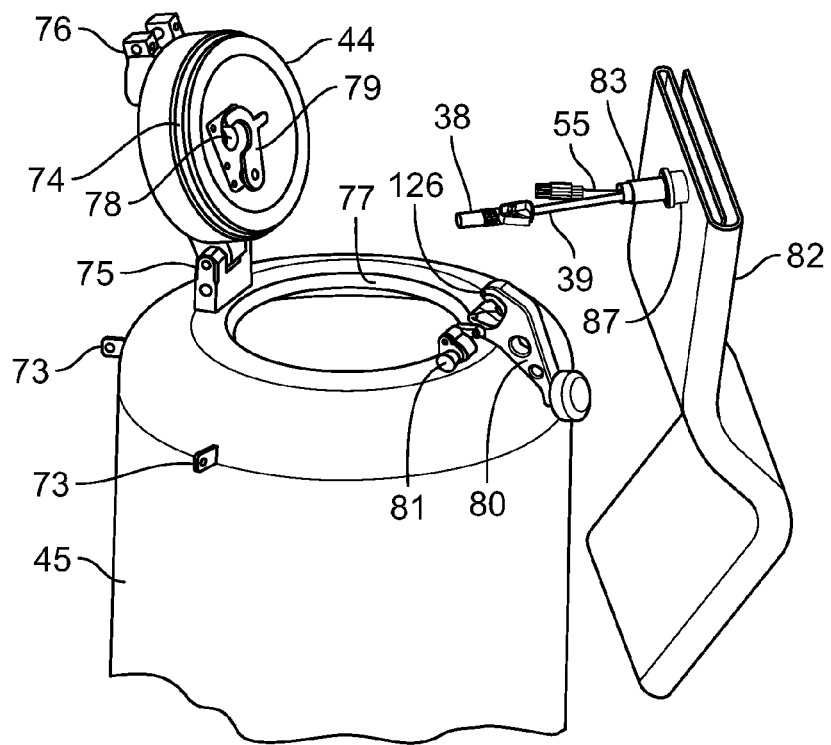
FIG. 3A is a perspective view of a pressurized container with an open lid.
Figure 3B:
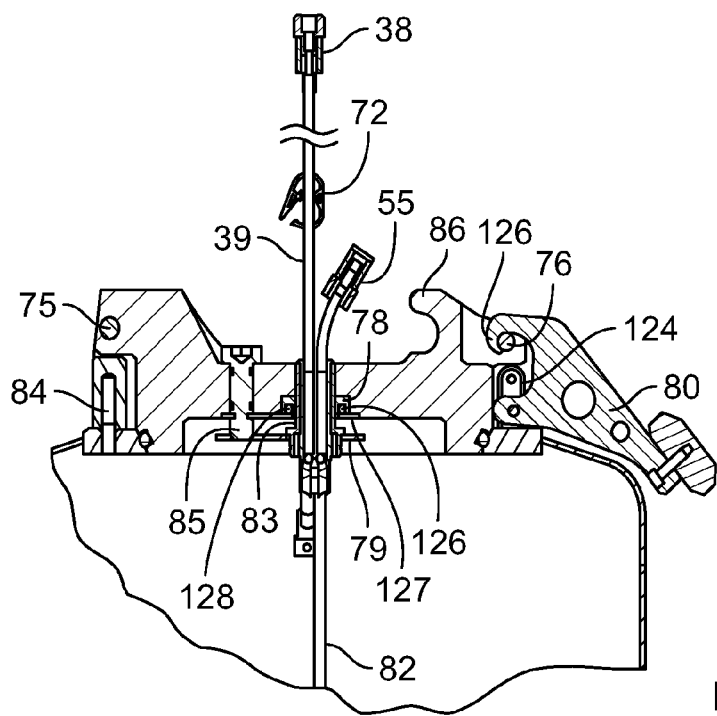
FIG. 3B is a partial cross-sectional view of the transport carriage and container with the lid closed.

FIG. 3 schematically shows the pressurized container (45) with open lid (44) and a connector receptacle (78), through which the cylindrical bag connector (83) is inserted and held by means of movable connector locking device (79) and holding slot (87).

In order for a positive sealing with good sliding properties to be possible between the connector (83) and connector receptacle seal (78), preferably the seal (78) consists of a Teflon insert (128), which is pressed with an O-ring (126) and a pressure plate (127) against connector (83) in such a manner that the aforementioned objectives are achieved.

A positive and sealing joining of the lid (44) to the pressurized container (45) is achieved on the one hand by lid seal (74) and the conical seal mounting (77) in the pressurized container opening in the closed state.

For closing, hook (126) pulls the lid locking device (76) into position by means of locking device handle (80). Locking device safeguard (81) thereby locks in place behind the pivot joint (124). Lid clamping hinge (75) holds lid (44) in the open state in an upright position.

It shall be understood that the bag (41/82) is to be introduced into the container for this purpose. For vertical support, two lateral guides (73) are affixed to the pressurized container (45).

The compressed air supply (66) is affixed, for example, in the hinge area (75) by means of link (84).

Connector locking device (79) is to open from outside via a turning shaft (85) by means of a tool in the event of an error.

Likewise, in this figure the filling line (39) is depicted with connector (38), whereby said filling line is to be connected to the link (35) in the filling process. Clamp (72) can be closed after the filling process. For differentiation between the filling line (39) and the transfer line (55), these are equipped with different connectors and executed, as depicted, in different lengths.

Figure 4A:
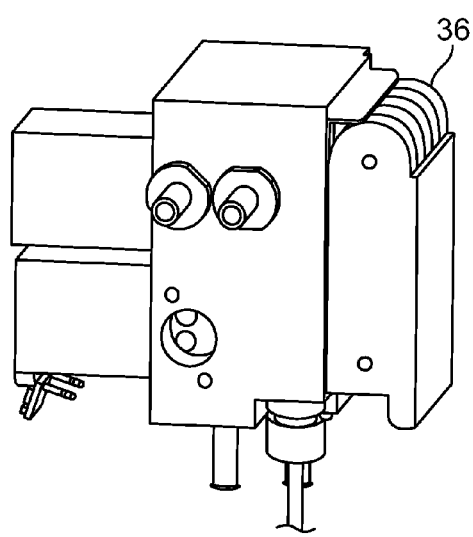
FIG. 4A is a perspective view of a flush solution link flap.
Figure 4B:
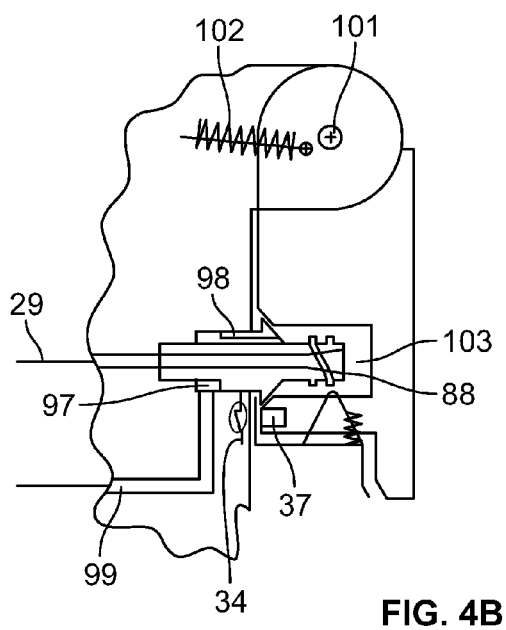
FIG. 4B is a schematic cross-sectional view of the flush solution link with flap in a closed position.
Figure 4C:
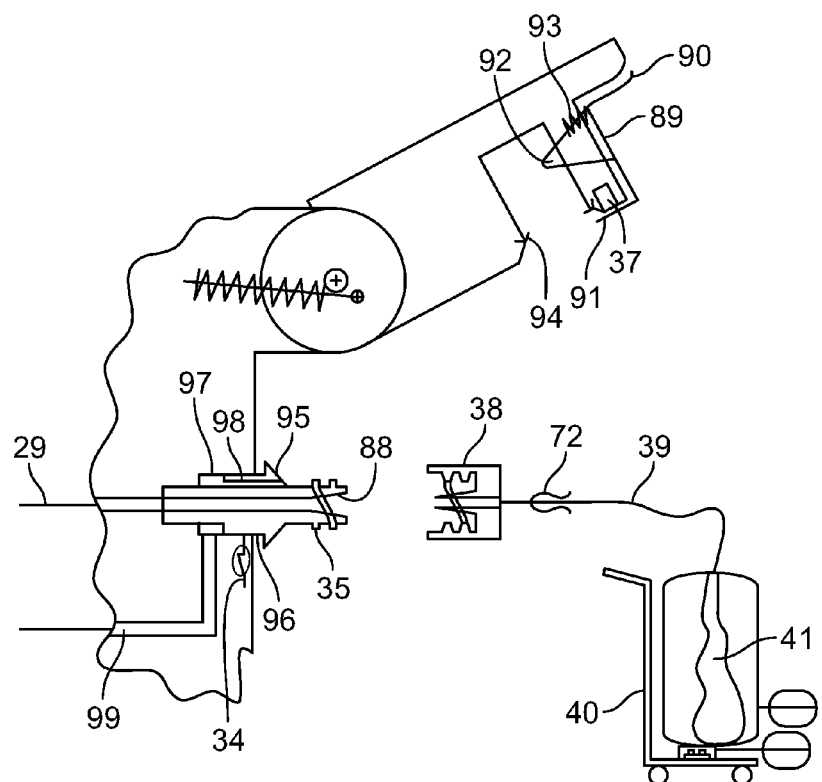
FIG. 4C is a schematic cross-sectional view of the flush solution link with flap in an open position.
Figure 5A:
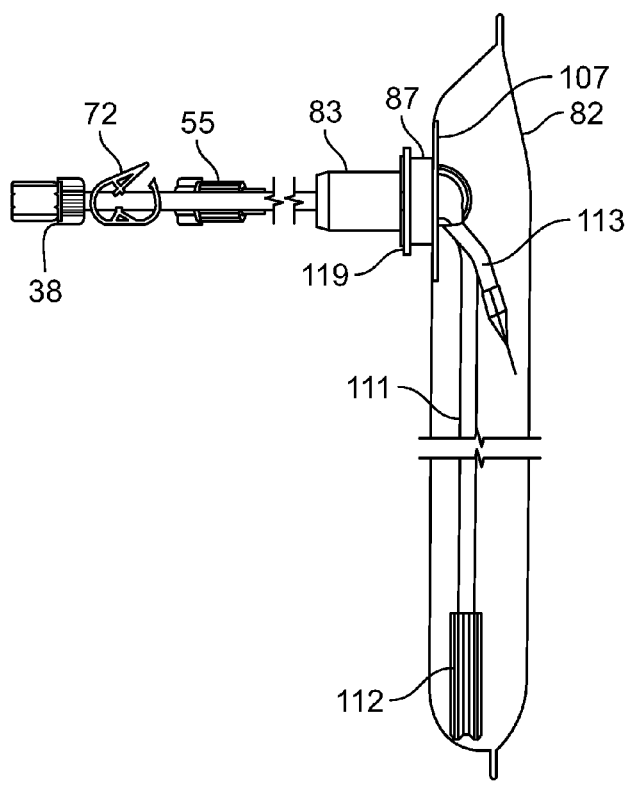
FIG. 5A is a side view of a concentrate bag and connectors.
Figure 5B:
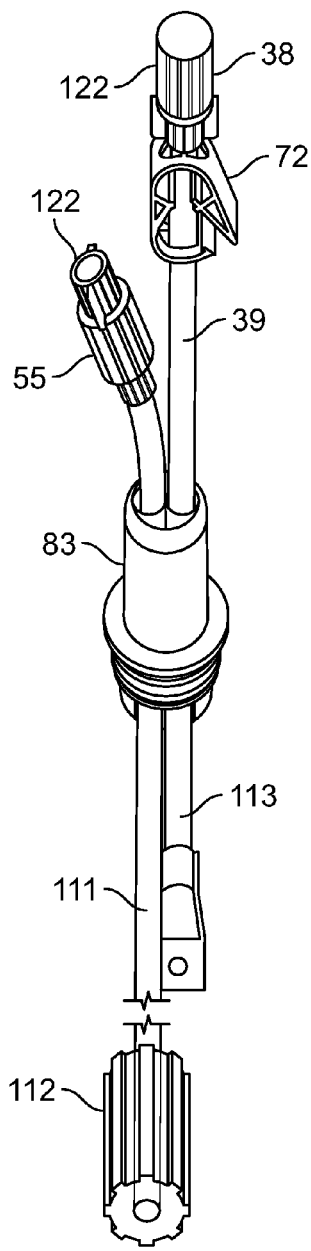
FIG. 5B is a perspective view of the concentrate bag connectors and lines.
Figure 5C:
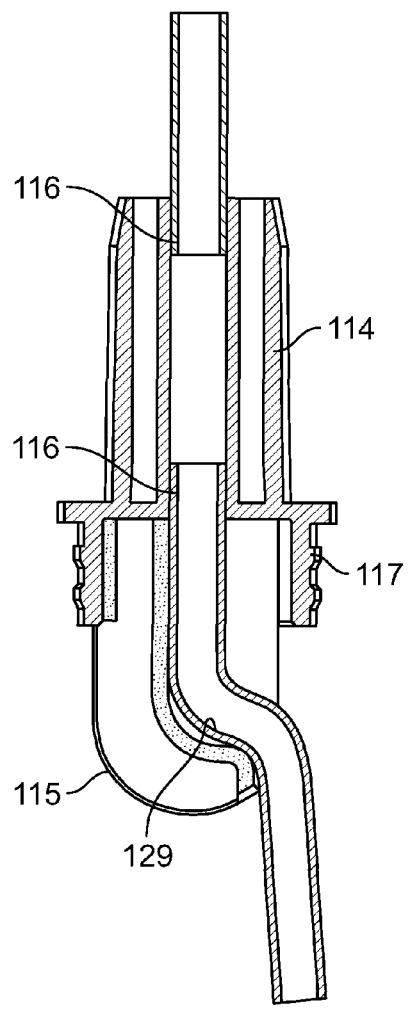
FIG. 5C is a cross-sectional view of the bag connector and lines.
Figure 5D:
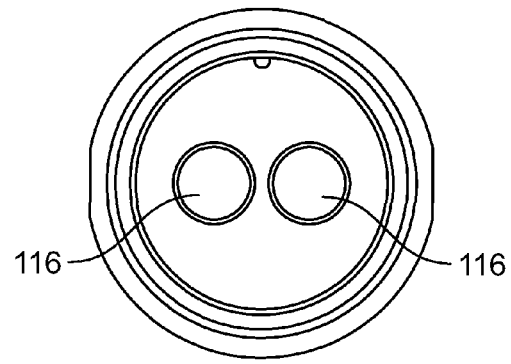
FIG. 5D is an end view of the bag connector.
Figure 5E:
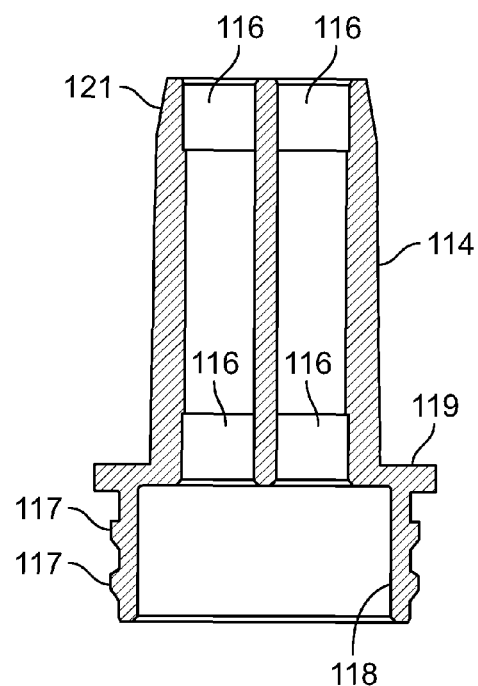
FIG. 5E is a cross-sectional view of the bag connector.
Figure 5G:
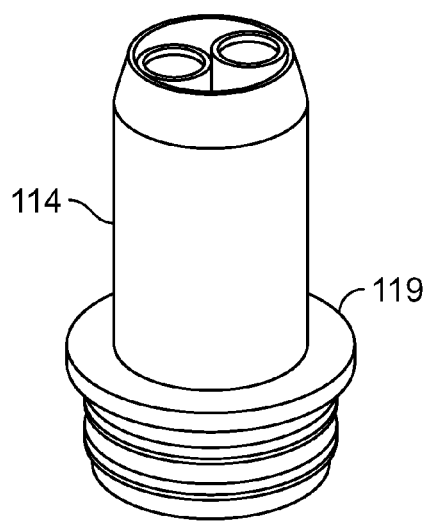
FIG. 5G is a partial cross-sectional view of a connector receptacle.
Figure 5G:
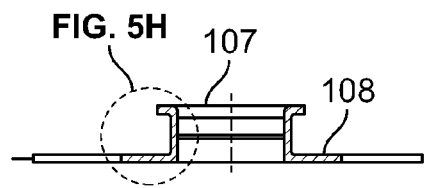
Figure 5F:
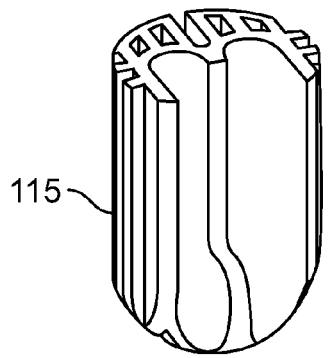
FIG. 5F is an exploded perspective view of the bag protector and bend protection.
Figure 5H:
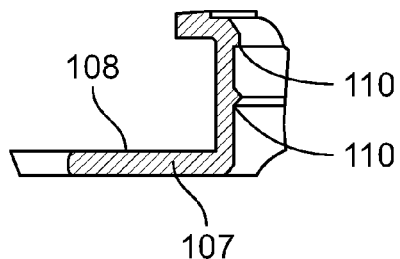
FIG. 5H is a detailed view of the circled area of FIG. 5g.
Figure 5I:
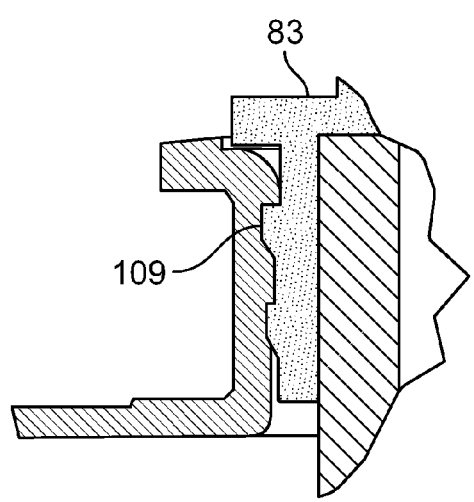
FIG. 5I is cross-sectional view of the bag connector and receptacle.
Figure 5J:
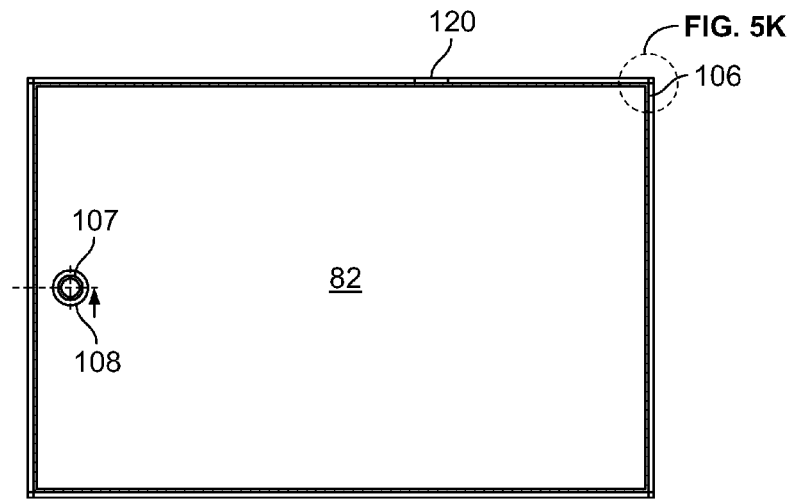
FIG. 5J is a plan view of the concentrate bag.
Figure 5K:
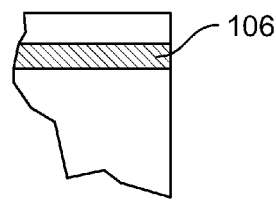
FIG. 5K is an edge detail of the circumferential bag welding.

FIG. 4 offers a perspective schematic view of the flush solution flap (36), whose opening, closing and excavation and cleaning process are described in the following.

Located in the flap (36) is a magnet (37) that activates a magnetic contact (34) when the flap is closed.

For flushing, the flap (36) is closed so that the flap locking device hook (91) snaps the flap locking device (89) into place in the locking collar (96) of the link connector (35).

By pressing back the locking device (89) over the pivot point (92) by means of flap locking device handle (90) the locking device spring (93) is compressed and the flap locking device hook (91) thereby releases the excavation process of the flap (36). The flap swivels upwards. This is supported by an excavation spring (102) which engages at the side of the flap pivot point (101).

For complete flushing of the connector (35), the seal (94) presses in a positive fit onto the outer cone (95) of the connector (35) when the flap is closed.

Via link (29) via the internal cone (88) the flush fluid penetrates to the flushing area (103) and from there via the circumferentially arranged flush bores (98) of the connector (35) into the annular gap (97) from which the flush drain (99) procedure takes place.

To rule out mix-ups during use, the technical execution of the flush solution links was designed to be different than those for the concentrate links.

Located under the flush solution flap (36) is a flush solution connector (35) executed, for example, with an internal cone (88) 1 to 16 and a double-threaded external screw thread 13×8 Located on the flush solution bag (41), which is executed as a disposable article, is the filing line (39) with disposable connector (38) which as a male connector is equipped, for example, with freely rotatable union nut with internal screw thread 13×8 and an internal outer cone 1 to 16 in such a way that in the coupled state a positive, sealing joining is guaranteed by the two cones and screw thread. A hose clip (72) can be mounted in the filling line (39).

FIG. 5 thereby schematically shows the flush solution bag (82) which consists of a multi-layer, toxicologically harmless material, preferably PE foil.

The bag (82) has a rectangular, welded contour into which on one side a bag and connector receptacle (107) is welded into the foil in a circular form. The connector receptacle (107) is internally radially provided with at least 2 latching teeth (110) into which the connector (83) is pressed in such a manner that a positive, sealing, non-detachable pressing action (109) is created.

In FIG. 5 the connector (83) is executed in two pieces, whereby one-piece, similar geometries are also possible in the framework of the invention. In the depicted version, the connector (83) consists of a front part (114) whose essential constituents are the hose gluing points (116) into which the transfer and filling lines are preferably glued internally and externally, as well as the collar (119) for the holding slot (87) and latching teeth (117).

For easier insertion into the connector receptacle (78) of the lid (44) the front part (114) comprises a side-cut (121). Towards the back a receptacle (118) for bend protection (115) of the internal lines (111/113) is provided.

In the installed state, the bag connector (83) is mounted vertically with connector locking device (79) in holding slot (87).

With the lid (44) closed, there is a twisting of the bag (82) by around 90° against the connector (83) and consequently also a positional change of the internal transfer (111) and filling line (113). The bend protection (115) comprises hose guides (129) that should prevent a possible buckling of the same.

The transfer line (111) terminates at the lower end with a hose weight (112), which has on all outer sides contours in order firstly to guarantee complete emptying of the bag when the foil is pressed together and secondly in order to counteract a possible upswing of the transfer line (111).

To avoid contact contamination, the connectors (55) and (38) can comprise protective caps (122) with openings for gassing for the purpose of sterility.

The foils of the bag (82) are circumferentially welded in such a way that a weld head of at least greater than 2 mm is present in order to avoid a rupture.

Already depicted in FIG. 3 is a possible folding of the bag (82) that facilitates simple insertion into the pressurized container opening (77).

Whereby bag (82) can also be executed in a contour or form other than that depicted in the description. It is consequently possible, e.g., to affix the two links of the connector (83) frontally, meaning to the upper side of the bag (82) or instead to do completely without the connector (83) and to weld the links (39/55) directly into the top side. In this case a different positive sealing should be used.

Furthermore, if an additional pump, not depicted in the figure, is used, circulation of the fluid located in the bag via the two links of the connector (83) can be realized in order to improve or prepare, as the case may be, homogeneity, temperature or a fluid already located in the bag. The links are thereby to be correspondingly connected to the flow direction of the pump or corresponding to the purpose.

Figure 6:
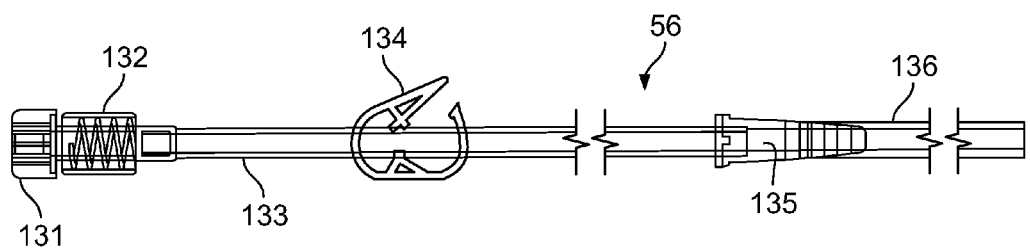
FIG. 6 is a diagram of a transition system.

FIG. 6 shows the diagram of a transition system which with its connector (132) can be adapted to the transfer link (55) and to which the conical link piece (134) or a silicon hose piece (136) following the same is to be linked to an endoscopy or also flush system common in surgery.

The cone (135) facilitates the receiving of different silicon hose diameters (136) in order to link different systems used in surgery.

The hose clip (134) can advantageously also be executed as a roller clamp for the regulation of the flush flow.

The length of the hose (133) is arbitrary and its diameter should be adapted to the desired flush flow, whereby a hose diameter (133) of approximately 7 mm, which is glued into connector (132), was selected for the shown system.

For reasons of sterility link (132) was equipped with a gasable cap (131).

| Legend |
| --- |
| 1. Preliminary filtration |
| 2. RO system |
| 3. Permeate ultra/sterile filter |
| 4. Disinfection unit |
| 5. Permeate release valve |
| 6. Air pressure infeed, air pump |
| 7. Air intake filter |
| 8. Temperature regulator |
| 9. Heater |
| 10. Overtemperature protection |
| 11. Permeate supply line |
| 12. Mixing unit |
| 13. Temperature regulator/display |
| 14. Pressure sensor |
| 15. Mixing chamber |
| 16. Redundant conductivity measurement/temperature display |
| 17. Concentrate flush valve |
| 18. Flush line |
| 19. Concentrate flap detector |
| 20. Concentrate flap |
| 21. Magnet |
| 22. Concentrate bag link connector with double-threaded internal screw thread and internal outer cone |
| 23. Concentrate pump |
| 24. Concentrate bag connector with breaking cone with double-threaded external screw thread and internal cone |
| 25. Concentrate bag link |
| 26. Concentrate bag |
| 27. Concentrate bag hanger |
| 28. Concentrate bag scale |
| 29. Flush solution line |
| 30. Sterile filter 2 |
| 31. Flush solution by-pass valve |
| 32. Sampling point |
| 33. Flush solution release valve |
| 34. Flush solution flap detector |
| 35. Flush solution connector with internal cone and double-threaded external screw thread |
| 36. Flush solution flap |
| 37. Magnet |
| 38. Flush solution bag connector with outer cone and internal screw thread |
| 39. Flush solution filling line |
| 40. Mobile flush solution container |
| 41. |
| 42. |
| 43. Flush solution container scale |
| 44. Lid |
| 45. Pressurized container |
| 46. Transport carriage |
| 47. Pressure regulation unit |
| 48. Compressed air connector |
| 49. Hose extension |
| 50. Pressure regulator |
| 51. Emergency off |
| 52. Pressure limiting valve |
| 53. Pressure manometer |
| 54. Pressure sensor |
| 55. Transfer link with double-threaded external screw thread, internal cone and sealing flap |
| 56. Transition system |
| 57. OP application |
| 58. Electronics |
| 59. Thermal sensor |
| 60. Filling station |
| 61. Push and pull handle |
| 62. Electronics for transport carriage |
| 63. Infusion pole |
| 64. Signal light display |
| 65. Communication display for pressure, temperature, filling level |

| Legend |
| --- |
| 66. Compressed air hose connection |
| 67. Disinfecting/cleaning agent canister |
| 68. RO membrane |
| 69. Feed tank |
| 70. Pump with drive |
| 71. Concentrate scale extension piece with bag hanging hooks |
| 72. Hose clip |
| 73. Lateral guide for pressurized container |
| 74. Lid seal |
| 75. Lid clamping hinge |
| 76. Lid locking bolt |
| 77. Pressurized container opening with conical seal mounting |
| 78. Connector receptacle with internal pre-strsssed sliding seal |
| 79. Connector locking device |
| 80. Locking device handle with hook |
| 81. Locking device safeguard |
| 82. Flush solution bag |
| 83. Bag connector |
| 84. Compressed air supply |
| 85. Turning shaft locking device with hexagonal socket |
| 86. Excavation handle |
| 87. Holding slot |
| 88. Flush solution connector internal cone |
| 89. Flap locking device |
| 90. Flap locking device handle |
| 91. Flap locking device hook |
| 92. Flap locking device pivot point |
| 93. Flap locking device spring |
| 94. Flap seal |
| 95. Seal counter-bearing |
| 96. Locking collar |
| 97. Flush flow annular gap |
| 98. Flush bores |
| 99. Flush drain |
| 100. Drain |
| 101. Flush solution flap turning shaft |
| 102. Excavation spring |
| 103. Flushing area |
| 104. Mobile flush solution container bottom plate |
| 105. Rollers |
| 106. Circumferential welded bag seam |
| 107. Connector receptacle |
| 108. Circular point at which foil is welded on |
| 109. Connector pressing |
| 110. Latching teeth at connector receptacle |
| 111. Internal transfer line |
| 112. Weight |
| 113. Internal filling line with optional non-return valve |
| 114. Bag-connector, front part |
| 115. Bag-connector, bend protection |
| 116. Hose gluing points |
| 117. Latching teeth for bag receptacle |
| 118. Bend protection receptacle |
| 119. Holding slot collar |
| 120. Bag lettering |
| 121. Connector insertion chamfer |
| 122. Sterility sealing caps |
| 123. Pivot point for pivot joint |
| 124. Pivot joint |
| 125. Chamfer, pivot joint |
| 126. O-ring |
| 127. Pressure plate |
| 128. Teflon insert |
| 129. Hose guides |
| 130. Lid locking device hook |
| 131. Gassing cap with external screw thread 13 × 8 |
| 132. Patient connector with union nut, internal screw thread 13 × 8 and outer cone 1/16 |
| 133. Hose, approx. 7 mm |
| 134. Hose clip |
| 135. Cone, corrugated (5-10 mm) |
| 136. Silicon hose piece |

The invention claimed is:
1. A system for storing and applying flush solutions, the system comprising:

a flush solution bag, and a rigid container for arranging the flush solution bag therein, the rigid container having a swiveling lid, the swiveling lid having a connector receptacle through which a bag connector can be stuck, the connector receptacle being mounted to the bag connector by means of a connector locking device and a holding slot, the connector locking device being movable with respect to the connector receptacle, a filling line running through and extending outwardly from the bag connector, the filling line being provided at an end with a link connector, a link connector of a mixing unit, the mixing unit being external to and separate from the rigid container, the link connector of the mixing unit having a first end and an opposed second end, the first end extending from the mixing unit, the first end being fixed to the mixing unit and removably connectable to the end of the link connector of the filling line, and a swiveling flush solution flap connected to the mixing unit via a pivot point that is disposed on the mixing unit, the flush solution flap being disposed with respect to the link connector of the mixing unit such that, when the first end of the link connector of the mixing unit and the end of the link connector of the filling line are not connected to one another, the flush solution flap can pivot between an open state, wherein the first end of the link connector of the mixing unit is exposed, and a closed state covering an opening at the first end of the link connector of the mixing unit wherein the first end of the link connector of the mixing unit is closed, wherein the flush solution flap is configured such that when the flush solution flap is in the closed state, a flushing area is defined that extends between the flush solution flap and the opening of the link connector of the mixing unit, and further extends between the flush solution flap and an outer portion of the first end of the link connector of the mixing unit, wherein the flushing area is sealed, and wherein a flushing fluid line is in fluid communication with the opening of the link connector of the mixing unit via the second end of the link connector of the mixing unit wherein the flushing fluid line discharges into the flushing area in such a way that flushing fluid can clean the link connector of the mixing unit on the inside and outside.

2. The system according to claim 1,
wherein the rigid container comprises a pressurized container.

3. The system according to claim 1,
wherein the flush solution bag is formed from a multi-layer polyethylene (PE) foil that is welded at edges of the flush solution bag.

4. The system according to claim 1,
wherein the bag connector has a front part into which the filling line and a transfer line are glued.

5. The system according to claim 1,
wherein the bag connector comprises the holding slot,
wherein the connector locking device comprises a latch of the swiveling lid,
wherein the holding slot runs around an outside circumference of the bag connector, and
wherein the holding slot engages the latch therein.

6. The system according to claim 1, further comprising:
an essentially sleeve-shaped connector receptacle welded into a lateral surface of the flush solution bag, the essentially sleeve-shaped connector receptacle being provided with internal latching teeth, and
wherein the bag connector has a backward sleeve-shaped section with latching teeth, wherein said backward sleeve-shaped section can be pressed into the essentially sleeve-shaped connector receptacle in such a manner that a positive, sealing and non-detachable pressing action results.

7. The system according to claim 6, further comprising:
bend protection arranged in the backward sleeve-shaped section of the bag connector, wherein the bend protection comprises hose guides.

8. The system according to claim 1, further comprising:
a hose weight mounted at an end of a transfer line in the flush solution bag,
wherein an outside of the hose weight includes a longitudinally directed ribbed contour.

9. The system according to claim 1, further comprising:
a pump arranged to be connectable to the filling line and a transfer line in order to circulate the fluid contained in the flush solution bag.

10. The system according to claim 1,
wherein the rigid container comprises a pressurized container, and
further comprising:
a transport carriage for the pressurized container that has a pressure regulation unit for regulating the pressure in the pressurized container.

* * * * *